United States Patent [19]

Powell

[11] Patent Number: 5,049,130
[45] Date of Patent: Sep. 17, 1991

[54] SYSTEM AND METHOD FOR PRESSURE FILLING OF CATHETERS

[75] Inventor: Philip E. Powell, Palo Alto, Calif.

[73] Assignee: Cardiovascular Imaging Systems, Inc., Sunnyvale, Calif.

[21] Appl. No.: 290,217

[22] Filed: Dec. 23, 1988

[51] Int. Cl.⁵ .................. A61M 29/02; A61B 8/12
[52] U.S. Cl. .................................. 604/96; 604/103; 606/194; 128/662.06
[58] Field of Search .............. 128/662.06, 4, 6; 604/96–103; 606/194

[56] References Cited

U.S. PATENT DOCUMENTS

| 2,936,761 | 5/1960 | Snyder | 604/96 |
| 3,983,879 | 10/1976 | Todd | 604/96 |
| 4,324,235 | 4/1982 | Beran | 128/207.15 |
| 4,466,443 | 8/1984 | Utsugi | 128/4 |
| 4,637,396 | 1/1987 | Cook | 604/99 |
| 4,638,805 | 1/1987 | Powell | 606/192 |
| 4,692,200 | 9/1987 | Powell | 606/192 |
| 4,715,378 | 12/1987 | Pope, Jr. et al. | 606/194 |
| 4,717,381 | 1/1988 | Papantonakos | 604/95 |
| 4,752,286 | 6/1988 | Okada | 604/96 |
| 4,762,129 | 8/1988 | Bonzel | 604/96 |
| 4,811,737 | 3/1989 | Rydell | 606/194 |
| 4,821,722 | 4/1989 | Miller et al. | 604/96 |
| 4,938,220 | 7/1990 | Mueller, Jr. | 604/96 X |
| 4,955,895 | 9/1990 | Sugiyama et al. | 606/194 |

FOREIGN PATENT DOCUMENTS 234951  9/1987  European Pat. Off. .

Primary Examiner—Francis Jaworski
Attorney, Agent, or Firm—Townsend and Townsend

[57] ABSTRACT

A vascular catheter includes an elongate catheter tube having proximal and distal ends as well as a lumen extending between said ends. A catheter housing secured to the distal end of the catheter tube is covered by an elastic sheath. A vent path formed in the catheter tube housing is normally blocked by the sheath, but fluid being fed into the catheter lumen may be flushed through the housing by employing a sufficiently high pressure.

23 Claims, 2 Drawing Sheets

SYSTEM AND METHOD FOR PRESSURE FILLING OF CATHETERS

BACKGROUND OF THE INVENTION

1. Field of the Invention

The present invention relates generally to the construction of catheters having liquid-filled lumens. More particularly, the present invention relates to a catheter design and method for filling a sealed catheter lumen which minimize the retention of gas bubbles within the liquid-filled lumen.

Arteriosclerosis is a pandemic health problem which can cause myocardiol infarction (heart attack) and a variety of other circulatory diseases. Arteriosclerosis is characterized by vascular constrictions, generally referred to as stenoses, which result from the build-up of atheroma and plaque on the interior wall of the blood vessel. Initially, atheroma is soft and has a relatively low density. Over time, however, the atheroma calcifies into a hard plaque having a high density which can significantly occlude a blood vessel. Moreover, once plaque forms, platelets can aggregate on the diseased blood vessel wall, forming clot and thrombus which further occlude the lumen.

Over the past decade, numerous approaches for reducing and removing such vascular constrictions have been proposed, including balloon angioplasty where a balloon-tipped catheter is used to dilate a region of stenosis, atherectomy where a blade or cutting bit is used to sever and remove the obstruction, and laser angioplasty where laser energy is used to ablate at least a portion of the obstruction. Embolectomy is a surgical technique where a balloon-tipped catheter is surgically introduced to a blood vessel and used to draw stenotic material back to the surgical incision from where it is removed.

In performing such therapeutic techniques, a vascular catheter carrying an appropriate device at its distal end is percutaneously or surgically introduced to the blood vessel. The distal tip of the catheter is then guided to the region of stenosis while the surgeon follows its progress using a fluoroscope. Once in position, the therapeutic procedure is performed and the catheter is subsequently removed.

A major limitation on the performance of such procedures has been a lack of detailed visual information. Although fluoroscopy can generally reveal the position and extent of blockage, little information is provided on the nature of the stenotic material and the boundary location between the stenotic material and the blood vessel wall. Without such information, it is difficult to tailor the treatment protocol to the individual patient.

Thus, there exists a need for intravascular imaging systems which can provide detailed visual information on the nature and extent of the stenotic blockage. Such a system is disclosed in U.S. Pat. No. 4,794,931, the disclosure of which is incorporated herein by reference. The disclosed system provides internal viewing of the blood vessel wall, allowing the surgeon to closely observe the obstruction and select the most appropriate treatment modality. The viewing further allows the surgeon to direct the treatment to the particular site within the region of stenosis where it will be most effective. Finally, the surgeon can immediately review the results of the treatment, allowing assessment and an immediate determination of whether further treatment is appropriate.

The imaging system in the aforementioned patent application employs a vascular catheter having an ultrasonic transducer in its distal tip. When configured for imaging, the catheter tip will be sealed and filled with a liquid medium to provide for propagation of the ultrasonic signal. Normally, the tip will be filled through an axial lumen which extends to the distal tip. The sealed nature of the tip, however, makes it difficult to adequately flush the lumen and distal tip in order to substantially eliminate the presence of air bubbles. Even very small air bubbles which would present no danger of air embolism can significantly deteriorate propagation of an ultrasonic signal.

Thus, it would be desirable to provide catheter designs which allow for filling of the catheter without substantial retention of air bubbles. It would be particularly desirable to provide catheters and methods for filling catheters which allow for venting and flushing of the catheter lumen leading to the distal tip which houses the ultrasonic transducer.

2. Description of the Background Art

U.S. Pat. No. 4,638,805, describes a balloon dilation catheter, where the balloon terminates in a small-diameter passage at its distal end. The passage is sized to permit the venting of gases while substantially inhibiting the flow of liquids therethrough. Published European application, 234,951 is the equivalent of U.S. Pat. No. 4,794,931 discussed above.

SUMMARY OF THE INVENTION

According to the present invention, a catheter comprises an elongate catheter tube having a proximal end, a distal end, and at least one axial lumen extending between the proximal and distal ends. The catheter lumen will be open at the proximal end but substantially sealed elsewhere along its length, except that at least one vent path will be provided through the catheter wall, usually at or near the distal end. The vent path, however, will normally be covered and sealed by an elastic sheath which circumscribes and conforms to the exterior of the catheter tube. The sheath is composed of an elastic material having an elastic modulus and wall thickness which allow for expansion in response to a predetermined internal threshold pressure within the lumen. Such internal pressure is applied against the sheath through the axial lumen and vent path in order to expand the sheath to provide an opening (i.e., vent) to the exterior. In this way, the venting of the lumen can be accomplished by introducing a liquid medium to the open proximal end of the lumen at a pressure above the threshold pressure. As the pressure in the lumen is lowered below the threshold pressure, the distal end of the catheter again becomes sealed against intrusion from the exterior.

In the exemplary embodiment, the catheter is a vascular imaging catheter, of the type described in U.S. Pat. No. 4,794,931 the disclosure of which has been previously incorporated herein by reference. The vascular imaging catheter includes a housing formed at the distal end of a catheter tube, where the interior of the housing is able to receive fluid from the catheter tube lumen. Within the housing, an ultrasonic transducer is mounted opposite a rotating mirror which acts to transversely reflect an ultrasonic signal emanating from the transducer. In order to enhance transmission of the ultrasonic signal to the exterior, it is necessary that the housing be completely filled with an appropriate liquid medium, such as normal saline or sterile water. Heretofore, it has been difficult to fill the interior of the housing with suitable liquid media because of the tendency of air bubbles to remain within the housing. The transducer, mirror, and other interior appurtenances, tend to entrap air bubbles and render their removal difficult.

The ultrasonic imaging catheter incorporating the present invention overcomes these problems by providing a large circumferential gap in the housing, which gap serves two functions. First, the gap in the housing provides a clear acoustic path for transmission and reception of the ultrasonic signal being reflected by the mirror. Second, the gap provides a large vent path which allows a relatively high volume purge of the interior with the liquid medium introduced through the catheter lumen. The elastic sheath preferably covers the entire housing, extending over the gap in the housing wall. The sheath may be formed from a variety of materials, particularly elastomers which provide minimal attenuation of the ultrasonic signal. In the preferred embodiment, the sheath is sealed to the housing at each end, and a plurality of apertures are provided to allow escape of the liquid medium when the sheath is expanded by the medium pressure.

Although the present invention is particularly useful in the construction of ultrasonic imaging catheters, as just described, it may also find use in a wide variety of other applications whenever it is desired to fill an internal lumen of a sealed catheter tube with a liquid medium. The catheter vent system will also be useful for delivering drugs and other substances, such as contrast medium, to locations within a patient's vascular system. For example, the catheter lumen may be initially flushed with a liquid medium containing the substance of interest (or the substance dissolved or suspended in a suitable medium). The catheter may then be emplaced at a desired location within the vascular system and the substance released by applying pressure to the open proximal end of the lumen.

DESCRIPTION OF THE SPECIFIC EMBODIMENTS

Figure 1:
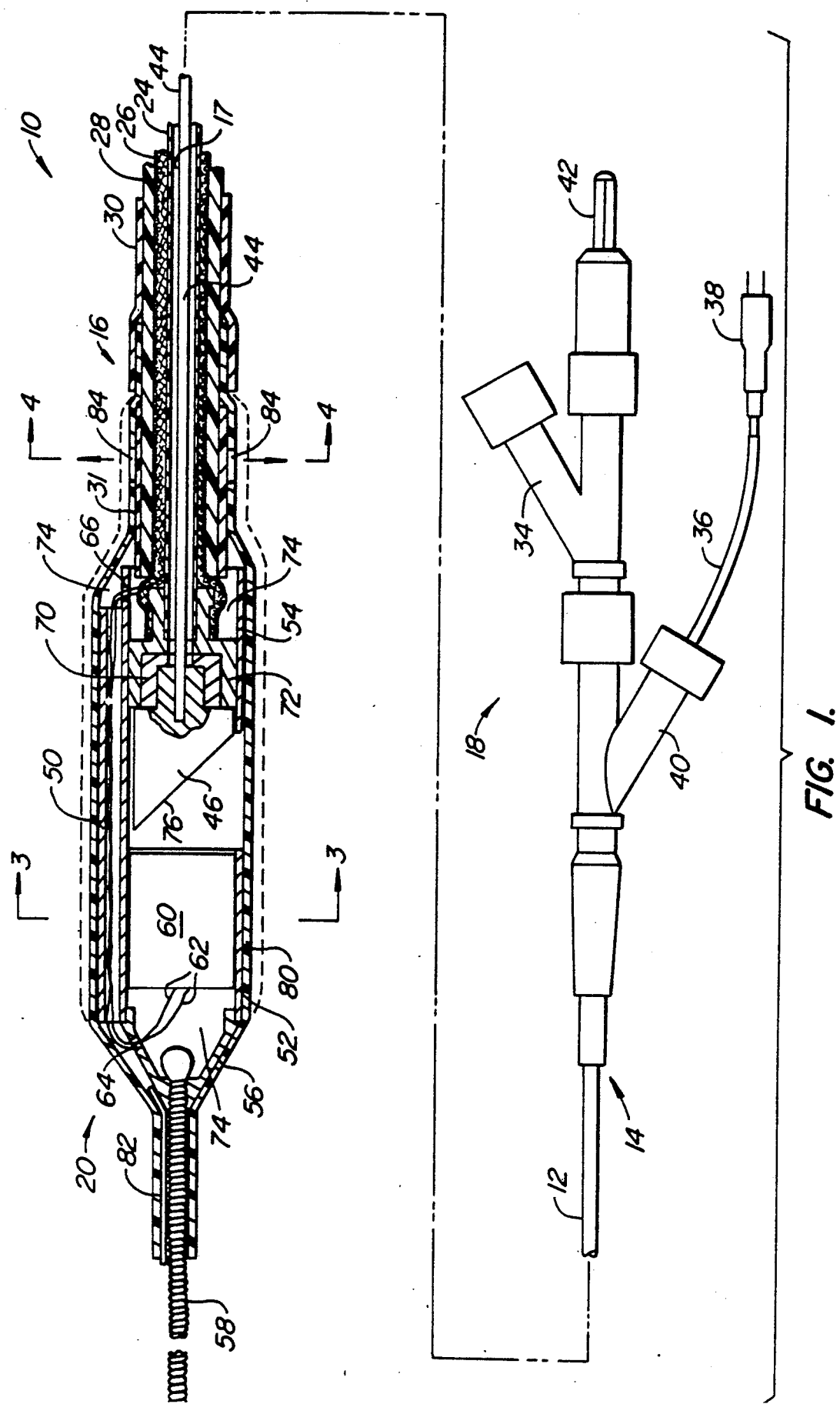
FIG. 1 is an elevational view of the catheter constructed in accordance with the principles of the present invention, with the distal end shown in section.

Catheters constructed in accordance with the principles of the present invention will comprise an elongate catheter tube having a proximal end, a distal end, and an axial lumen extending therebetween and an elastic sheath circumscribing the catheter tube at some point to cover a vent path formed in the tube wall. The catheter will normally be a medical catheter, particularly including vascular catheters, urethral catheters, endoscopes, nasogastric catheters, intrauterine catheters, and the like. The exemplary catheter is a vascular imaging catheter employing an ultrasonic scanning system in its distal end.

For vascular catheters, the catheter tube will comprise a highly flexible body capable of insertion into and manipulation within a patient's vascular system. The dimensions of the catheter will depend on use, with length varying widely, typically being between about 40 cm and 150 cm, usually being between about 50 cm and 100 cm. The catheter tube diameter may also vary widely, typically being between about 2 F (French) and about 12 F, usually being between about 5 F and 9 F, and more usually varying from about 6 F to 8 F (1 French =0.013 inches), with catheters for peripheral arteries generally being larger. The flexible catheter tube may be composed of a wide variety of biologically compatible materials, particularly being made from elastomers such as silicone rubber, natural rubber, polyvinyl chloride, polyurethanes, polyesters, polytetrafluoroethylene, and the like. Frequently, the catheter tube may be a composite material having a reinforcement material incorporated therein in order to achieve the desired strength, flexibility, and toughness. Suitable catheter tubes will normally be formed by extrusion, with one or more integral lumens being provided. The catheter diameter can then be modified by heat expansion and shrinkage using conventional techniques. The construction of suitable vascular catheters is well described in the patent and medical literature.

The catheter tube will normally include a housing at its distal end. The housing may be formed integrally with the catheter tube or may be a separate structure which is secured to the distal end of the catheter tube, where the separate structure may be formed from the same or different material. As used hereinafter and in the claims, the term "catheter tube" will generally include the housing as present in the catheter structure. Thus, vent paths formed in the housing will be considered within the catheter tube wall.

Frequently, it will be desirable to construct the housing of the present invention out of a rigid material, such as a metal or a rigid plastic, although it is possible that the housing will itself be flexible. Normally, a working device will be disposed within the housing, where a connection between the working device and the proximal end of the catheter is provided through the axial lumen. In the exemplary embodiment, an ultrasonic imaging system is disposed within the distal housing of the catheter.

The catheter lumen will generally be sealed along its length, but will include at least one port at its proximal end to allow access thereto. In addition to such opening(s) at the proximal end, the catheter lumen will be connected to at least one vent path at a point located distally of the proximal end (either through the catheter tube wall or through the distal housing), where the vent path provides for purging of fluids introduced through the proximal opening(s) as described in more detail hereinafter.

Desirably, the vent path will be sufficiently large to allow a substantial flow of liquid therethrough, which in turn will provide vigorous purging of the catheter lumen (and housing) in order to remove substantially all air bubbles. Usually, each vent path will have a cross-sectional area equal to at least about 0.25 of the lumen area, more usually being at least about 0.5 of the lumen area, preferably being at least about equal to the lumen area, and more preferably being at least three times the lumen area. The open area of the vent path is defined as that area which is covered by the sheath in order to prevent outflow.

The elastic sheath will circumscribe the catheter tube and/or housing at the location of the vent path(s), and will be constricted about the catheter tube to seal the opening defined by the vent path. The sheath will block the vent path both to prevent inflow from the exterior of the sheath into the lumen and outflow from the lumen to the exterior. In this way, the lumen is effectively isolated from its surroundings, except through the port(s) provided at the proximal end. The sheath may be formed integrally with the catheter tube, e.g., by co-extrusion of two layers, but will more usually be formed over the catheter tube by heat shrinkage.

The elastic sheath, however, will be formed to have a desired modulus of elasticity so that internal pressure within the catheter tube lumen will be able to expand the sheath to allow outward flow through the vent path. The modulus of elasticity and sheath vent configuration will be chosen to provide such opening at a preselected threshold pressure, typically being within the range from about 2 to 200 psig, more typically being within the range from about 5 to 50 psig. For internal pressures below such a threshold value, the sheath will remain in place to block outward fluid flow. By providing internal pressures well above the threshold value, very large flow rates through the catheter lumen may be provided in order to enhance removal of internal air bubbles. Once the pressure is reduced, the elastic shield will again constrict around the vent path opening, sealing the tube from the exterior.

The sheath may be formed from a variety of elastomeric materials, particularly thermoplastics, thermosetting elastomers, such as polyethylene, silicone rubbers, polyvinylchloride, polyurethanes, polyesters, natural rubbers, copolymers, coextrusions, and the like, with silicone rubber and polyethylene being preferred. The thickness of the sheath material will vary depending on the desired elastic modulus and acoustic properties, typically being in the range from about 0.0001 to 0.1 inches, more typically being in the range from about 0.0005 to 0.002 inches, measured after forming. Typically, the modulus of elasticity of the sheath material will be in the range from about 10 to 10,000 psi, usually being in the range from about 30 to 500 psi, more usually being in the range from about 25 to 50 psi. Conveniently, the sheath may be formed on the catheter using conventional heat expansion and shrinkage techniques.

Figure 2:
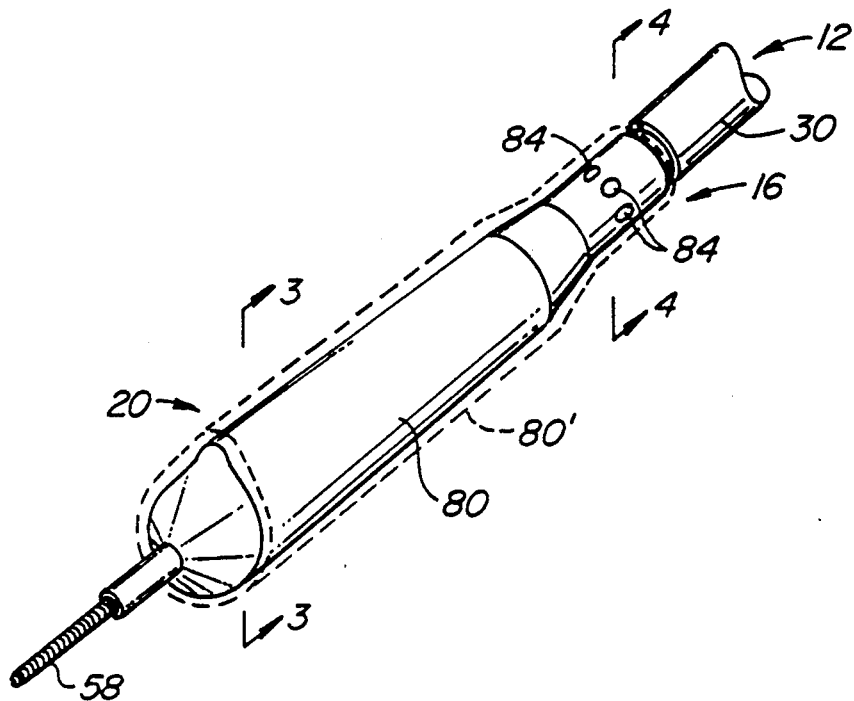
FIG. 2 is a detail view of the distal end of the catheter of FIG. 1.
Figure 3:
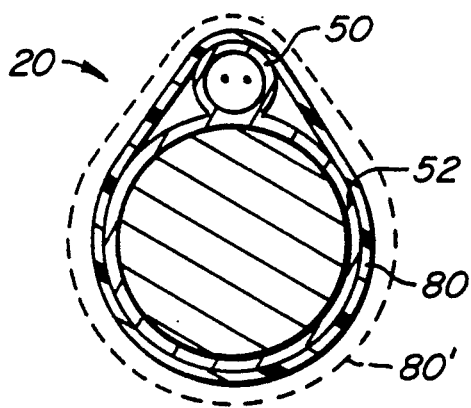
FIG. 3 is a cross-sectional view taken along lines 3—3 in FIGS. 1 and 2.
Figure 4:
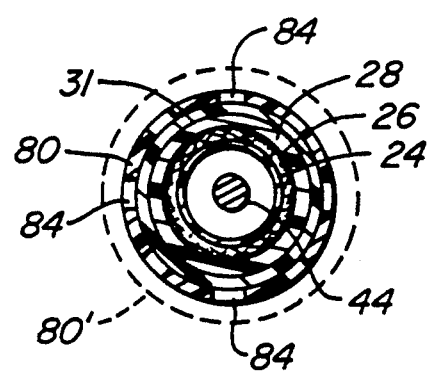
FIG. 4 is a cross-sectional view of the catheter of the present invention taken along lines 4—4 in FIGS. 1 and 2.

Referring now to FIGS. 1-4, an exemplary vascular imaging catheter 10 constructed in accordance with the principles of the present invention will be described in detail. The catheter 10 includes an elongate flexible catheter tube 12 having a proximal end 14, a distal end 16 and an axial lumen 17 extending from the proximal to distal end. A proximal housing 18 is secured to the proximal end of catheter tube 12, while a catheter housing 20 is secured to the distal end of the catheter tube.

The catheter tube 12 is a laminant structure including an interior liner 24, typically composed of a polyimide material, a shield layer 26, typically composed of a stainless steel braid, and a tubular body 28, typically composed of an extruded polyethylene formed over the shield layer 26 by heat shrinkage. A jacket layer 30 will typically be formed over the tubular body 28. The jacket layer 30 may also be composed of polyethylene and formed by heat shrinkage over the tubular body 28.

The proximal housing 18 includes a side port 34 which is connected to the proximal end of lumen 17. Side port 34 will be used to provide the liquid medium which is introduced into the lumen 17 and eventually into the interior of catheter housing 20, as described in more detail hereinafter. Housing 18 further includes an electrical cable 36 having a plug 38 at its end. The cable 36 enters the housing 18 through branch 40 and is connected with wires which extend through the catheter tube to an ultrasonic transducer, as will be described in more detail hereinafter. Housing 18 further includes a drive shaft 42 which is connected to drive cable 44 which extends through the entire length of lumen 17 and is connected to a rotating mirror 46 in catheter housing 20.

The major structural element of catheter housing 20 is a rigid connector tube 50 having a forward ring 52 and a rearward ring 54 depending therefrom. Typically, the connector tube 50 and rings 52 and 54 will be integrally formed from a single material, although this is not necessary. Conveniently, the material may be a metal, such as stainless steel, although other rigid materials, such as a rigid plastic might also find use. The connector tube 50, however, should be able to provide shielding for wires connecting the ultrasonic transducer, as described in more detail hereinafter.

An end plug 56 is attached to the forward end of forward ring 52 and is secured to a guidewire 58 at its forward end. An ultrasonic transducer 60 is mounted within the forward ring 52, and wires 62 extend from the transducer 60 through a port 64 in the end plug 56 and subsequently through the interior lumen of connector tube 50. At the rear end of connector tube 50, the wires 62 extend through a port 66 in rearward ring 54, after which the wires are routed through the shield layer 26. The wires 62 are then routed back to the proximal housing 18 between the shield layer 26 and the interior liner 24. Within the proximal housing 18, the wires are connected to the cable 36. In this way, the transducer 60 may be plugged into an appropriate receiver transmitter, as described in more detail in U.S. Pat. No. 4,794,931, the disclosure of which has previously been incorporated herein by reference.

The rotating mirror 46 is mounted within a bearing cup 70, which in turn is mounted within a connector member 72. The connector is secured about its outer periphery to the rearward ring 54 of the catheter housing 20, and is further attached at its rear end to the inner liner 24 and the shield layer 26 of the catheter tube 12. In this way, the catheter housing 20 is connected to the catheter tube 12. A filler material 74, such as an ultraviolet (UV) cured epoxy, is provided both at the forward end of the catheter housing between the end plug 56 and the ultrasonic transducer 60 as well as at the rear end of the housing about the connector member 72.

The mirror 64 is adapted to rotate within the space between the forward ring 52 and rearward ring 54. As the mirror includes an inclined forward surface 76, it will be appreciated that ultrasonic energy emanating from the transducer 60 will be received in the axial direction and reflected a substantially transverse direction. As illustrated, inclined surface 76 has a 45° inclination relative to the axial direction. The precise angle of inclination, of course, can be varied somewhat in order to change the location of the visual sweep. In any event, the ultrasonic energy reflected by the mirror 46 will pass through the gap between the forward ring 52 and rearward ring 54 so that it will be substantially unimpeded.

The gap between forward ring 52 and rearward ring 54 also serves as the vent path for the lumen 17 of the catheter 10. An elastic sheath 80 circumscribes the catheter housing 20 of catheter 10, covering the vent path defined between the forward ring 52 and rearward ring 54 of the housing. The elastic sheath 80 will be formed of an acoustically transparent material, conveniently a low crystalline polyethylene, which will serve to physically isolate the interior of the catheter housing 20 while being substantially free from impeding passage of ultrasonic energy. The sheath 80 extends from the proximal end of housing 20, where it is formed over end plug 56 and further over a portion of guidewire 58. Conveniently, a distal vent tube 82 may be provided parallel to the guidewire 58 to allow for bleeding of the interior of the housing forward of the end plug 56. The vent tube 82 has a very small diameter which will allow for passage of gases, while substantially inhibiting the flow of liquids, such as the liquid medium which is used to fill housing 18. Thus, the vent tube 82 is not a vent path as defined herein, but rather is similar to the type of vent described in U.S. Pat. No. 4,638,805, the disclosure of which is incorporated herein by reference.

The rearward or proximal end of the elastic sheath 80 extends over the distal end of catheter tube 12 for a preselected distance. The distance is not critical, and will typically be in the range from about 0.1 to 3 cm, more typically being in the range from about 0.3 to 2 cm. The proximal end of the sheath 80 is secured to the exterior of catheter 12 by the jacket layer 30. Typically, the jacket layer 30 will be placed over the proximal end of the sheath 80 and secured by heat shrinkage. Optionally, the sheath 80 may be adhesively bonded, heat staked, ultrasonically welded, or radio frequency (RF) welded to the catheter tube 12 to prevent migration during use. In this way, the sheath 80 is secured at either end to the catheter housing 20 and will generally prevent flow in and out of the interior of the housing.

In order to provide for the desired purging of the interior of housing 20, a plurality of apertures 84 are formed in the sheath 80 immediately proximal to the housing. Normally, the sheath 80 in the vicinity of apertures 84 will be tightly constricted about spacer layer 31 of catheter tube 12. In this configuration, flow in and out of the catheter housing 20 is entirely restricted. By increasing the internal pressure within the housing, however, the elastic sheath 80 will be expanded to the position shown in broken line and indicated by reference numeral 80'. In this configuration, an open path from the vent path between rings 52 and 54 will exist to the apertures 84, so that fluid within the housing 20 may be purged.

Thus, the housing 20 may be filled and purged with a desired liquid medium by introducing such medium through the side port 34 and proximal housing 18. The liquid medium will flow from the distal end of lumen 17 through the gap between mirror 46 and bearing cup 70 to enter the interior of housing 20. From there, it will pass through the annular gap caused by expansion of sheath 80 and outward through the ports 84.

Conveniently, the sheath 84 will be transparent so that the housing 20 may be visually inspected for air bubbles. Typically, a flow of liquid medium having a volume from about 5 to 20 cc, more typically from about 10 to 15 cc, will be required for flushing the catheter prior to use. Alternatively, a flow of liquid medium at a pressure of about 50 psi for a time period in the range from about 20 to 30 seconds will be sufficient. Once the catheter has been flushed with a suitable liquid medium, it will be ready for use. Suitable liquid media include, sterile water and normal saline. The liquid medium may be introduced to the catheter housing 20 through side port 34 in a conventional manner, typically using a syringe or other pressure device.

The catheter 10 just described may further be employed for deliverying a drug or other substance, such as contrast medium, to a region of interest within the patient's vascular system. The liquid medium used to fill the catheter will contain the substance of interest. Exemplary drugs include anti-coagulants, such as heparin, as well as clot-dissolving drugs, such as tissue plasminogen activator (TPA), urokinase, and streptokinase. Exemplary contrast media include Hypaque®. The substance may then be delivered by raising the pressure within the lumen 17 above the threshold value to cause a predetermined volume of the liquid medium to be released through the vent path at the distal end of the catheter 10. Conveniently, by introducing liquid to the proximal end of lumen 17, an equal volume of liquid medium will be released from the distal vent.

Although the foregoing invention has been described in some detail by way of illustration and example for purposes of clarity of understanding, it will be obvious that certain changes and modifications may be practiced within the scope of the appended claims.

What is claimed is:

1. A catheter comprising:
   an elongate catheter tube having an interior, an exterior surface, a proximal end, a distal end, and at least one lumen extending through the interior from said proximal end to said distal end, said lumen being connected to a vent path which extends from the interior to the exterior surface near the distal end and which is sufficiently large to allow liquid flow therethrough; and
   an elastic sheath conforming to the exterior surface near the distal end of the catheter tube and preventing fluid flow through the vent path, said sheath having a modulus of elasticity and geometry selected to allow expansion of the sheath in response to a threshold fluid pressure within the lumen, said expansion of the sheath allowing gas and liquid fluid flow from the lumen through the vent path.

2. A catheter as in claim 1, wherein the sheath includes at least one port therethrough, which port is sufficiently large to allow liquid flow therethrough and connects to the flow path when the sheath is expanded.

3. A catheter as in claim 1, wherein the sheath has a modulus of elasticity in the range from about 10 to 10,000 psi.

4. A catheter as in claim 3, wherein the sheath is composed of polyethylene.

5. A catheter as in claim 1, wherein the vent path has a cross-sectional area equal to at least about 0.25 of the lumen area.

6. A vascular catheter comprising:
   al elongate flexible catheter tube having an interior, an exterior surface, a proximal end, a distal end, and at least one lumen extending through the interior from said proximal end to said distal end;
   a housing secured to the distal end of the catheter tube and having an exterior surface and an interior which is connected to said lumen, wherein a vent path extends from the interior to the exterior surface, said vent path being sufficiently large to allow liquid flow therethrough;
   an elastic sheath conforming to the exterior surface and extending over at least a portion of said housing to prevent fluid flow from the interior of the housing through the vent path to the exterior, said sheath having a modulus of elasticity selected to allow expansion of the sheath in response to a threshold fluid pressure within the housing interior, said expansion allowing fluid flow from the housing interior to the exterior.

7. A vascular catheter as in claim 6, wherein the housing is generally cylindrical and axially aligned with the catheter tube, said housing having an aperture which is sufficiently large to allow liquid flow and forms a portion of the vent path.

8. A vascular catheter as in claim 7, wherein the sheath extends over the aperture.

9. A vascular catheter as in claim 8, wherein each end of the sheath is sealed to the catheter tube and the sheath includes at least one port therethrough, which port is axially offset from the vent path and provides a fluid flow path when the sheath is expanded.

10. A vascular catheter as in claim 6, wherein the sheath has a modulus of elasticity in the range from about 10 to 10,000 psi.

11. A vascular catheter as in claim 10, wherein the sheath is composed of polyethylene.

12. A vascular catheter as in claim 6, further comprising an ultrasonic transducer within the housing and means for directing a signal from the transducer in a transverse direction.

13. A vascular catheter as in claim 12, wherein an annular gap is formed in the housing adjacent the means for directing the ultrasonic signal, said gap defining the vent path and allowing outward propagation of the ultrasonic signal.

14. A catheter as in claim 6, wherein the vent path has a cross-sectional area equal to at least about 0.25 of the lumen area.

15. A method for filling a catheter lumen with liquid medium, said catheter lumen being substantially sealed but including a vent path at its distal end which opens when pressure in the lumen exceeds a preselected threshold value and closes when the pressure falls below said threshold value, said method comprising:
introducing the liquid medium to the catheter lumen at a pressure which exceeds the threshold value, whereby liquid and gas fluids vent from the distal vent, at least until substantially all vapor is bled from the lumen.

16. A method as in claim 15, wherein the liquid medium is sterile water or normal saline.

17. A method as in claim 15, wherein the preselected threshold pressure value is in the range from about 2 to 200 psig.

18. A method as in claim 15, wherein at least about 5 cc of liquid medium is vented from the catheter lumen.

19. A method as in claim 15, wherein the vent path is sealed by an elastic sheath when the pressure in the lumen is below the threshold value, said sheath having a modulus of elasticity and geometry selected so that it will expand to open the vent path when the lumen pressure exceeds the threshold value.

20. A method as in claim 15, further comprising the step of discharging liquid medium from the catheter lumen through the distal vent while the catheter is located within a patient's vascular system.

21. A method as in claim 20, wherein the volume of discharged liquid medium is equal to a predetermined volume introduced to the lumen at the proximal end of the catheter.

22. A method as in claim 20, wherein the liquid medium is contrast medium.

23. A method as in claim 20, wherein the liquid medium contains an anti-coagulant or a clot-dissolving drug.

* * * * *